United States Patent
Dias et al.

(10) Patent No.: US 9,783,473 B2
(45) Date of Patent: Oct. 10, 2017

(54) PROCESS FOR PRODUCTION OF HEXAMETHYLENEDIAMINE FROM CARBOHYDRATE-CONTAINING MATERIALS AND INTERMEDIATES THEREFOR

(71) Applicant: Rennovia, Inc., Santa Clara, CA (US)

(72) Inventors: Eric L. Dias, Belmont, CA (US); James A. W. Shoemaker, Gilroy, CA (US); Thomas R. Boussie, Menlo Park, CA (US); Vincent J. Murphy, San Jose, CA (US)

(73) Assignee: Rennovia Inc., Santa Clara, CA (US)

( * ) Notice: Subject to any disclaimer, the term of this patent is extended or adjusted under 35 U.S.C. 154(b) by 0 days.

(21) Appl. No.: 15/195,349

(22) Filed: Jun. 28, 2016

(65) Prior Publication Data

US 2017/0050906 A1    Feb. 23, 2017

Related U.S. Application Data

(63) Continuation of application No. 14/687,894, filed on Apr. 15, 2015, now abandoned, which is a continuation of application No. 14/290,869, filed on May 29, 2014, now Pat. No. 9,035,109, which is a continuation of application No. 13/739,975, filed on Jan. 11, 2013, now Pat. No. 8,853,458.

(60) Provisional application No. 61/588,093, filed on Jan. 18, 2012.

(51) Int. Cl.
| | |
|---|---|
| C07C 29/157 | (2006.01) |
| C07D 307/46 | (2006.01) |
| C07D 307/50 | (2006.01) |
| C07C 29/132 | (2006.01) |
| C07D 307/48 | (2006.01) |
| C07C 29/17 | (2006.01) |
| C07C 29/141 | (2006.01) |
| C07C 209/16 | (2006.01) |

(52) U.S. Cl.
CPC .......... *C07C 29/157* (2013.01); *C07C 29/132* (2013.01); *C07C 29/141* (2013.01); *C07C 29/175* (2013.01); *C07C 209/16* (2013.01); *C07D 307/46* (2013.01); *C07D 307/48* (2013.01); *C07D 307/50* (2013.01)

(58) Field of Classification Search
None
See application file for complete search history.

(56) References Cited

U.S. PATENT DOCUMENTS

| | | | |
|---|---|---|---|
| 2,082,025 A | 6/1937 | Peters, Jr. | |
| 2,750,394 A | 6/1956 | Peniston | |
| 2,754,330 A | 7/1956 | Schreyer | |
| 2,917,520 A | 12/1959 | Cope | |
| 2,929,823 A | 3/1960 | Garber et al. | |
| 3,040,062 A | 6/1962 | Hales | |
| 3,070,633 A | 12/1962 | Torleif et al. | |
| 3,083,236 A | 3/1963 | Utne et al. | |
| 3,118,912 A | 1/1964 | Smith | |
| 3,215,742 A | 11/1965 | Horlenko et al. | |
| 3,268,588 A | 8/1966 | Horlenko et al. | |
| 3,270,059 A | 8/1966 | Winderl et al. | |
| 3,985,814 A | 10/1976 | Dougherty | |
| 4,064,172 A | 12/1977 | Dewdney et al. | |
| 4,339,387 A | 7/1982 | Fleche et al. | |
| 4,400,468 A | 8/1983 | Faber | |
| 4,533,743 A | 8/1985 | Medeiros et al. | |
| 4,590,283 A | 5/1986 | Gaset et al. | |
| 4,740,605 A | 4/1988 | Rapp | |
| 4,912,237 A | 3/1990 | Zeitsch | |
| 4,971,657 A | 11/1990 | Avignon et al. | |
| 5,151,543 A | 9/1992 | Ziemecki | |
| 5,969,194 A | 10/1999 | Hara et al. | |
| 6,331,651 B1 | 12/2001 | Ostermaier | |
| 6,426,438 B1 | 7/2002 | Fischer et al. | |
| 6,518,440 B2 | 2/2003 | Lightner | |

(Continued)

FOREIGN PATENT DOCUMENTS

| | | |
|---|---|---|
| CA | 2097812 A1 | 6/1992 |
| EP | 2390247 A1 | 11/2011 |

(Continued)

OTHER PUBLICATIONS

International Search Report and Written Opinion received for PCT Patent Application No. PCT/US2013/021315, mailed Apr. 12, 2013, 15 pages.

(Continued)

*Primary Examiner* — Brian J Davis
(74) *Attorney, Agent, or Firm* — Rennovia IP Department

(57) ABSTRACT

Processes are disclosed for the conversion of a carbohydrate source to hexamethylenediamine (HMDA) and to intermediates useful for the production of hexamethylenediamine and other industrial chemicals. HMDA is produced by direct reduction of a furfural substrate to 1,6-hexanediol in the presence of hydrogen and a heterogeneous reduction catalyst comprising Pt or by indirect reduction of a furfural substrate to 1,6-hexanediol wherein 1,2,6-hexanetriol is produced by reduction of the furfural substrate in the presence of hydrogen and a catalyst comprising Pt and 1,2,6-hexanediol is then converted by hydrogenation in the presence of a catalyst comprising Pt to 1,6 hexanediol, each process then proceeding to the production of HMDA by known routes, such as amination of the 1,6 hexanediol. Catalysts useful for the direct and indirect production of 1,6-hexanediol are also disclosed.

27 Claims, No Drawings

(56) References Cited

U.S. PATENT DOCUMENTS

| | | |
|---|---|---|
| 6,706,932 B1 | 3/2004 | Konishi et al. |
| 6,743,928 B1 | 6/2004 | Zeitsch |
| 7,449,609 B2 | 11/2008 | Haunert et al. |
| 7,579,490 B2 | 8/2009 | Sanborn et al. |
| 7,994,347 B2 | 8/2011 | Lilga et al. |
| 8,367,851 B2 | 2/2013 | Lilga et al. |
| 8,742,144 B2 | 6/2014 | Lilga et al. |
| 8,846,984 B2 | 9/2014 | Allgeier et al. |
| 8,846,985 B2 | 9/2014 | Allgeier et al. |
| 8,853,458 B2 | 10/2014 | Dias et al. |
| 8,859,826 B2 | 10/2014 | Allgeier et al. |
| 8,884,036 B2 | 11/2014 | De Silva et al. |
| 8,889,912 B2 | 11/2014 | Allgeier et al. |
| 8,889,922 B2 | 11/2014 | Allgeier et al. |
| 8,962,894 B2 | 2/2015 | Allgeier et al. |
| 9,018,423 B2 | 4/2015 | Allgeier et al. |
| 9,035,109 B2 | 5/2015 | Dias et al. |
| 9,181,157 B2 | 11/2015 | Allgeier et al. |
| 9,518,005 B2 | 12/2016 | Dias et al. |
| 2003/0144552 A1 | 7/2003 | Boschat et al. |
| 2006/0128844 A1 | 6/2006 | Sanborn et al. |
| 2007/0287845 A1 | 12/2007 | Lilga et al. |
| 2008/0207958 A1 | 8/2008 | Haunert et al. |
| 2009/0177018 A1 | 7/2009 | Suzuki et al. |
| 2010/0317069 A1 | 12/2010 | Burk et al. |
| 2013/0172578 A1 | 7/2013 | Allgeier et al. |
| 2013/0172580 A1 | 7/2013 | Ritter et al. |
| 2013/0172629 A1 | 7/2013 | Allgeier et al. |
| 2013/0184495 A1 | 7/2013 | Dias et al. |
| 2013/0231505 A1 | 9/2013 | Allgeier et al. |
| 2013/0289311 A1 | 10/2013 | Allgeier et al. |
| 2013/0289312 A1 | 10/2013 | Allgeier et al. |
| 2013/0289318 A1 | 10/2013 | Allgeier et al. |
| 2013/0289319 A1 | 10/2013 | Allgeier et al. |
| 2013/0331606 A1 | 12/2013 | Dias et al. |
| 2014/0051872 A1 | 2/2014 | Blank et al. |
| 2014/0275638 A1 | 9/2014 | Huber et al. |
| 2014/0309461 A1 | 10/2014 | Yoshida et al. |
| 2015/0099903 A1 | 4/2015 | Allgeier et al. |
| 2016/0023975 A1 | 1/2016 | Allgeier et al. |

FOREIGN PATENT DOCUMENTS

| | | |
|---|---|---|
| FR | 2663933 A1 | 1/1992 |
| FR | 2664273 A1 | 1/1992 |
| FR | 2669635 A1 | 5/1992 |
| GB | 591858 A | 9/1947 |
| GB | 600871 A | 4/1948 |
| GB | 876463 A | 9/1961 |
| JP | 2008143798 A | 6/2008 |
| JP | 2009-46417 A | 3/2009 |
| WO | 93/16034 A1 | 8/1993 |
| WO | 96/18603 A1 | 6/1996 |
| WO | 2011/149339 A1 | 12/2011 |
| WO | 2013/101968 A1 | 7/2013 |
| WO | 2013101969 A1 | 7/2013 |
| WO | 2013101970 A1 | 7/2013 |
| WO | 2013101977 A1 | 7/2013 |
| WO | 2013/163540 A1 | 10/2013 |
| WO | 2013163547 A1 | 10/2013 |
| WO | 2013163556 A1 | 10/2013 |
| WO | 2013163561 A1 | 10/2013 |
| WO | 2014004867 A1 | 1/2014 |
| WO | 2014152366 A1 | 9/2014 |

OTHER PUBLICATIONS

Buntara et al., "Caprolactam from Renewable Resources: Catalytic Conversion of 5-Hydroxymethylfurfural into Caprolactone", Angew. Chem. Int. Ed., vol. 50, 2011, pp. 7083-7087.

Buntara et al., "Catalyst studies on the Ring Opening of Tetrahydrofuran—Dimethanol to 1,2,6-Hexanetriol", Catalysis Today, vol. 210, 2013, pp. 106-116.

Buntara et al., "From 5-Hydroxymethylfurfural (HMF) to Polymer Precursors: Catalyst Screening Studies on the Conversion of 1,2,6-hexanetriol to 1,6-hexanediol", Top Catal, vol. 55, 2012, pp. 612-619.

Koso et al., "Chemoselective Hydrogenolysis of Tetrahydrofurfuryl Alcohol to 1,5-Pentanediol", Chem. Communication, 2009, pp. 2035-2037.

Schiavo, "Catalytic Hydrogenation in Aqueous Medium of 5-Hydroxymethylfurfural and Precursor Sugars", Doctoral Dissertation, 1991, University of Lyon (English Abstract).

Schiavo et al., "Catalytic Hydrogenation in an Aqueous Medium of 5-Hydroxymethylfurfural and Precursor Sugars", Bull Soc Chim Fr, vol. 128, 1991, pp. 704-711 (English machine translation).

Schiavo et al., "Catalytic Hydrogenation in an Aqueous Medium of 5-Hydroxymethylfurfural and Precursor Sugars", Bull Soc Chim Fr, vol. 128, 1991, pp. 704-711.

Notice of Allowance received for U.S. Appl. No. 13/739,975, mailed on Feb. 19, 2014, 9 pages.

Besson, M. et al. (2014), "Conversion of Biomass into Chemicals over Metal Catalysts," Chem. Rev. 114 (3):1827-1870.

Chen, K., et al. (2010), "Chemoselective Hydrogenolysis of Tetrahydropyran-2-methanol to 1,6-Hexanediol over Rhenium-Modified Carbon-Supported Rhodium Catalysts," ChemCatChem 2:547-555.

Chia, M., et al. (2011), "Selective Hydrogeneolysis of Polyols and Cyclic Ethers over Bifunctional Surface Sites on Rhodium-Rhenium Catalysts," Journal American Chemical Society 133:126-75-12689.

Koso, S., et al. (2009), "Promoting Effect of Mo on the Hydrogenolysis of Tetrahydrofurfuryl Alcohol to 1,5-Pentanediol over Rh/SiO2," Journal of Catalysis 267:89-92.

Nakagawa, Y., et al. (2010), "Total Hydrogenation of Furan Derivatives Over Silica-Supported Ni—Pd Alloy Catalyst," Catalysis Communications 12:154-156.

Van Putten, R.J., et al. (2013), "Hydroxymethylfurfural, A Versatile Platform Chemical Made from Renewable Resources," Chem. Rev. 113:1499-1597.

PROCESS FOR PRODUCTION OF HEXAMETHYLENEDIAMINE FROM CARBOHYDRATE-CONTAINING MATERIALS AND INTERMEDIATES THEREFOR

CROSS-REFERENCE TO RELATED APPLICATION

This application is a continuation of U.S. application Ser. No. 14/687,894, filed Apr. 15, 2015, now abandoned, which is a continuation of U.S. application Ser. No. 14/290,869, filed on May 29, 2014, now issued as U.S. Pat. No. 9,035, 109, which is a continuation of U.S. application Ser. No. 13/739,975, filed Jan. 11, 2013, now issued as U.S. Pat. No. 8,853,458, which claims the benefit under 35 U.S.C. 119(e) of U.S. Provisional Application No. 61/588,093, filed on Jan. 18, 2012, the disclosures of which are hereby incorporated by reference in their entirety.

BACKGROUND

I. Field

The present disclosure relates generally to processes for conversion of a carbohydrate source to hexamethylenediamine and to intermediates useful for the production of hexamethylenediamine and other industrial chemicals. The present disclosure relates more specifically to chemocatalytic processes for the production of hexamtheylenediamine from a furfural substrate derived from a carbohydrate source, which substrate is converted to an intermediate comprising 1,6-hexanediol from which the hexamethylenediamine can be derived by chemocatalytic amination of the diol. The present invention is also directed to the production of 1,6-hexanediol from a furfural substrate in which at least a portion of the furfural substrate is converted to 1,2,6 hexanetriol, at least a portion of the hexanetriol is then converted to 1,6-hexanediol, and the 1,6 hexanediol is then converted to hexamethylenediamine by, for example, chemocatalytic amination of the diol. The present disclosure also relates to improved processes for the production of hexanediol from a furfural substrate.

II. Background

Hexamethylenediamine (HMDA) is a chemical intermediate primarily used in the production of nylon 6,6 via a condensation with adipic acid. HMDA is also used in the production of monomers for polyurethanes. Further, HMDA is used in the production of epoxy resins. Today, annual production of HMDA exceeds 3 billion pounds (avoir).

Crude oil is currently the source of most commodity and specialty organic chemicals. Many of these chemicals are employed in the manufacture of polymers and other materials. Desired chemicals include, for example, styrene, bisphenol A, terephthalic acid, adipic acid, caprolactam, hexamethylenediamine, adiponitrile, caprolactone, acrylic acid, acrylonitrile, 1,6-hexanediol, 1,3-propanediol, and others. Crude oil is first refined, typically by steam cracking, into hydrocarbon intermediates such as ethylene, propylene, butadiene, benzene, and cyclohexane. These hydrocarbon intermediates then typically undergo one or more catalytic reactions by various processes to produce these desired chemical(s).

HMDA is among those chemicals that continue to be produced commercially from oil via a multistep process. HMDA is typically produced from butadiene. Butadiene is typically produced from steam cracking of heavier feeds. The steam cracking of such feeds favors the production of butadiene, but also produces heavier olefins and aromatics. Thus, the butadiene resulting from the cracking step is typically extracted into a polar solvent from which it is then stripped by distillation. Butadiene is subjected to a hydrocyanation process in the presence of a nickel catalyst to produce adiponitrile. See, for example, U.S. Pat. No. 6,331, 651. HMDA is then produced typically by the hydrogenation of adiponitrile in the presence of a solid catalyst. See, for example, U.S. Pat. No. 4,064,172 (which discloses a process for producing HMDA by hydrogenating adiponitrile in the presence of an iron oxide catalyst) and U.S. Pat. No. 5,151,543 (which discloses that HMDA can be prepared by hydrogenating adiponitrile in the presence of a Raney nickel type catalyst doped with at least one metal element selected from Groups 4, 5, and 6 of the periodic table of the elements and, more recently, WO-A-93/16034 and WO-A-96/18603 (each of which discloses Raney nickel catalyst based processes for the production of HMDA from adiponitrile) and US Patent Application No. 2003/0144552 (which discloses a process for producing HMDA from adiponitrile in the presence of a particularly conditioned Raney nickel catalyst).

Notably, each of the above-mentioned documents directed to the production of HMDA acknowledges the need for improvement in the efficiency, selectivity and commercial competitiveness of such process. In fact, the need for improved or alternative commercial processes for the production of HMDA is exacerbated by the evolution of the chemical industry toward the use of lighter feeds which, when subjected to cracking, produce lesser amounts of butadiene and ultimately will lead to increased costs of producing HMDA and increased price volatility.

For many years there has been an interest in using biorenewable materials as a feedstock to replace or supplement crude oil. See, for example, Klass, Biomass for Renewable Energy, Fuels, and Chemicals, Academic Press, 1998, which is incorporated herein by reference.

Recently, HMDA and other chemicals used in the production of, among others materials, polymers such as nylon have been identified as chemicals that may be producible from biorenewable resources, particularly carbohydrate containing materials from which glucose can be obtained and used as the feedstock to manufacture such chemicals. See, for example, US 2010/0317069, which discloses biological pathways purported to be useful to produce, among other chemicals, caprolactam and HMDA.

To date, there is no commercially viable process for the production of HMDA from carbohydrate containing feedstocks. Given the shift away from the production of conventional, oil-derived starting materials such as butadiene, notwithstanding the continuing growth in the markets for nylons and polyurethanes, among other materials, derived at least in part from HMDA or derivatives thereof and the benefits attributable to the use of renewable feedstocks in lieu of petroleum derived feedstocks, new, industrially scalable methods for the selective and commercially-meaningful production of chemicals from polyhydroxyl-containing biorenewable materials (e.g., glucose derived from starch, cellulose or sucrose) to important chemical intermediates such as HMDA is compelling.

1,6-hexanediol (HDO) has been prepared from, for example, adipic acid, caprolactone and hydroxycaproic acid. See, for example, U.S. Pat. No. 5,969,194. Recently, a process for the production of 1,6-hexanediol from furfural derived from glucose has been disclosed in WO2011/ 149339. The '339 application provides a general description of at least a two step catalytic process for the production of HDO from 5-hydroxymethylfurfural (HMF): hydrogenation of HMF to 2,5-bis(hydroxymethyl)tetrahydrofuran (BHMTHF, also referred to as 2,5-tetrahydrofuran-dimethanol or THFDM) followed by hydrogenation of BHMTHF to 1,2,6-hexanetriol (HTO); and then hydrogenation of 1,2,6-hexanetriol to 1,6-hexanediol. The processes disclosed in the '339 application require at least two different catalyst systems to produce 1,6-hexanediol from HMF. Furthermore, the reported yields of HDO from HMF ranging from 4% (directly to HDO) to 22% (using a 3 step process: HMF to THFDM, THFDM to HTO, and then HTO to HDO). The low yields reported in the '339 application clearly demonstrate the need for development of alternative, more efficient processes for the production of HDO.

SUMMARY

Briefly, therefore, the present invention is directed to processes for preparing hexamethylenediamine from a carbohydrate source by converting a carbohydrate source to a furfural substrate; reacting at least a portion of the furfural substrate with hydrogen in the presence of a heterogeneous reduction catalyst to produce 1,6-hexanediol; and, converting at least a portion of the 1,6-hexanediol to hexamethylenediamine. The present invention is also directed to processes for preparing hexamethylenediamine from a carbohydrate source by converting a carbohydrate source to a furfural substrate; reacting at least a portion of the furfural substrate with hydrogen in the presence of a heterogeneous reduction catalyst comprising Pt to produce a reaction product comprising 1,2,6-hexanetriol; converting at least a portion of the 1,2,6-hexanetriol to 1,6-hexanediol; and converting at least a portion of the 1,6-hexanediol to hexamethylenediamine. In some embodiments, the heterogeneous reduction catalyst comprises Pt. In other embodiments, the heterogeneous reduction catalyst further comprises at least one metal selected from the group consisting of Mo, La, Sm, Y, W, and Re. In other embodiments, the step of converting at least a portion of the 1,2,6-hexanetriol to 1,6-hexanediol is conducted in the presence of hydrogen and a hydrogenation catalyst comprising Pt. In other embodiments, the yield of 1,6-hexanediol is at least about 40%. In other embodiments, the yield of 1,6-hexanediol is at least about 50%. In other embodiments, the yield of 1,6-hexanediol is at least about 60%. In other embodiments, the reaction of the furfural substrate with hydrogen is carried out at a temperature in the range of about 60° C. and about 200° C. and a pressure of hydrogen in the range of about 200 psig to about 2000 psig. In other embodiments, the furfural substrate is 5-hydroxymethylfurfural. In other embodiments, the carbohydrate source is glucose, fructose, or a mixture comprising glucose and fructose. In other embodiments, the catalyst further comprises a support selected from the group consisting of zirconias, silicas and zeolites. In other embodiments, the reaction of the furfural substrate with hydrogen is carried out at a temperature in the range of about 100° C. and about 180° C. and a pressure of hydrogen in the range of about 200 psig to about 2000 psig. In other embodiments, the hydrogenation catalyst comprises Pt and W supported on zirconia. The present invention is also directed to hexamethylenediamine produced by the processes of any of the above embodiments.

The present invention is also directed to processes for preparing 1,6-hexanediol from a carbohydrate source by converting the carbohydrate source to a furfural substrate; and, reacting at least a portion of the furfural substrate with hydrogen in the presence of a heterogeneous reduction catalyst comprising Pt to produce 1,6-hexanediol. The present invention is also directed to processes for preparing 1,6-hexanediol from a carbohydrate source by converting the carbohydrate source to a furfural substrate; reacting at least a portion of the furfural substrate with hydrogen in the presence of a Pt containing heterogeneous reduction catalyst to produce a reaction product comprising 1,2,6-hexanetriol; and, converting at least a portion of the 1,2,6-hexanetriol to 1,6-hexanediol. In some embodiments, the heterogeneous catalyst further comprises at least one metal selected from the group consisting of Mo, La, Sm, Y, W, and Re. In other embodiments, the step of converting at least a portion of the 1,2,6-hexanetriol to 1,6-hexanediol is conducted in the presence of hydrogen and a hydrogenation catalyst comprising Pt. In other embodiments, the hydrogenation catalyst is a supported heterogeneous catalyst. In other embodiments, the yield of 1,6-hexanediol from the furfural substrate is at least 40%. In other embodiments, the yield of 1,6-hexanediol from the furfural substrate is at least 50%. In other embodiments, the yield of 1,6-hexanediol from the furfural substrate is at least 60%. In other embodiments, the reaction of the furfural substrate with hydrogen is carried out at a temperature in the range of about 60° C. and about 200° C. and a pressure of hydrogen in the range of about 200 psig to about 2000 psig. In other embodiments, the furfural substrate is 5-hydroxymethylfurfural. In other embodiments, the carbohydrate source is glucose, fructose, or a mixture comprising glucose and fructose. In other embodiments, the catalyst further comprises a support selected from the group consisting of zirconias, silicas and zeolites. In other embodiments, the reaction of the furfural substrate with hydrogen to produce 1,2,6-hexanetriol is carried out at a temperature in the range of about 100° C. and about 140° C. and a pressure of hydrogen in the range of about 200 psig to about 1000 psig. In other embodiments, the catalyst comprises Pt and W supported on zirconia. The present invention is also directed to 1,6-hexanediol produced by the processes of any of the above embodiments.

The present invention is also directed to processes for preparing hexamethylenediamine from a carbohydrate source by: (a) converting a carbohydrate source to a furfural substrate; (b) reacting at least a portion of the furfural substrate with hydrogen in the presence of a heterogeneous reduction catalyst comprising Pt to a reaction product comprising 1,2,6-hexanetriol; (c) reacting at least a portion of the 1,2,6-hexanetriol with hydrogen in the presence of the heterogeneous reduction catalyst comprising Pt to produce 1,6-hexanediol; and (d) converting at least a portion of the 1,6-hexanediol to hexamethylenediamine, wherein steps b) and c) are conducted in a single reactor. The present invention is also directed to processes for preparing 1,6-hexanediol from a carbohydrate source by: (a) converting a carbohydrate source to a furfural substrate; (b) reacting at least a portion of the furfural substrate with hydrogen in the presence of a heterogeneous reduction catalyst comprising Pt to a reaction product comprising 1,2,6-hexanetriol; and (c) reacting at least a portion of the 1,2,6-hexanetriol with hydrogen in the presence of the heterogeneous reduction catalyst comprising Pt to produce 1,6-hexanediol, wherein steps b) and c) are conducted in a single reactor. In some embodiments, the heterogeneous reduction catalyst further comprises W. In other embodiments, steps (b) and (c) are carried out at a temperature in the range of about 60° C. and about 200° C. and a pressure of hydrogen in the range of about 200 psig to about 2000 psig. In other embodiments, the Pt containing catalysts of steps b) and c) are different and the temperatures and pressures at which steps b) and c) are conducted are substantially the same. In other embodiments, the temperatures and pressures at which steps b) and c) are conducted are different. In other embodiments, step b) is conducted at a temperature in the range of about 100° C. to about 140° C. and a pressure in the range of about 200 psig to about 1000 psig and step c) is conducted at a temperature in the range of about 120° C. to about 180° C. and a pressure in the range of about 200 psig to about 2000 psig. In other embodiments, the yield of 1,6-hexanediol from the furfural substrate is at least about 40%. In other embodiments, the yield of 1,6-hexanediol from the furfural substrate is at least about 50%. In other embodiments, the yield of 1,6-hexanediol from the furfural substrate is at least about 60%. In other embodiments, the carbohydrate source is glucose, fructose, or a mixture comprising glucose and fructose. In other embodiments, steps (b) and (c) are carried out in one reaction zone. In other embodiments, the catalyst comprises Pt and W supported on zirconia. The present invention is also directed to hexamethylenediamine produced by the processes of any of the above embodiments. The present invention is also directed to 1,6-hexanediol prepared by the process of any of the above embodiments.

The present invention is also directed to processes for preparing a compound of formula II

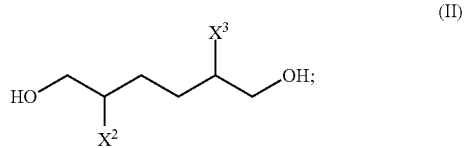

wherein each of $X^2$ and $X^3$ is selected from the group of hydrogen and hydroxyl; by converting a carbohydrate source to a furfural substrate; and, reacting at least a portion of the furfural substrate with hydrogen in the presence of a heterogeneous reduction catalyst comprising Pt to produce the compound of formula II. In some embodiments, the catalyst further comprises W. In other embodiments, the catalyst further comprises at least one metal selected from the group consisting of Mo, La, Sm, Y, W, and Re.

DETAILED DESCRIPTION

The following description sets forth exemplary methods, parameters and the like. It should be recognized, however, that such description is not intended as a limitation on the scope of the present invention.

In accordance with the present invention, applicants disclose processes for the chemocatalytic conversion of a furfural substrate, which may be derived from a carbohydrate source (e.g., glucose or fructose) to hexamethylenediamine, and intermediate processes and products along the pathway. In some embodiments, the processes are carried out by converting a carbohydrate source to a furfural substrate; reacting at least a portion of the furfural substrate with hydrogen in the presence of a heterogeneous reduction catalyst to produce 1,6-hexanediol; and, converting at least a portion of the 1,6-hexanediol to hexamethylenediamine. In other embodiments, the processes are carried out by converting a carbohydrate source to a furfural substrate; reacting at least a portion of the furfural substrate with hydrogen in the presence of a heterogeneous reduction catalyst comprising Pt to produce a reaction product comprising 1,2,6-hexanetriol; converting at least a portion of the 1,2,6-hexanetriol to 1,6-hexanediol; and converting at least a portion of the 1,6-hexanediol to hexamethylenediamine. In some embodiments, the processes are carried out by converting the carbohydrate source to a furfural substrate; and, reacting at least a portion of the furfural substrate with hydrogen in the presence of a heterogeneous reduction catalyst comprising Pt to produce 1,6-hexanediol. In other embodiments, the processes are carried out by converting the carbohydrate source to a furfural substrate; reacting at least a portion of the furfural substrate with hydrogen in the presence of a Pt containing heterogeneous reduction catalyst to produce a reaction product comprising 1,2,6-hexanetriol; and, converting at least a portion of the 1,2,6-hexanetriol to 1,6-hexanediol. In other embodiments, the processes are carried out by (a) converting a carbohydrate source to a furfural substrate; (b) reacting at least a portion of the furfural substrate with hydrogen in the presence of a heterogeneous reduction catalyst comprising Pt to a reaction product comprising 1,2,6-hexanetriol; (c) reacting at least a portion of the 1,2,6-hexanetriol with hydrogen in the presence of the heterogeneous reduction catalyst comprising Pt to produce 1,6-hexanediol; and (d) converting at least a portion of the 1,6-hexanediol to hexamethylenediamine, wherein steps b) and c) are conducted in a single reactor. In other embodiments, the processes are carried out by (a) converting a carbohydrate source to a furfural substrate; (b) reacting at least a portion of the furfural substrate with hydrogen in the presence of a heterogeneous reduction catalyst comprising Pt to a reaction product comprising 1,2,6-hexanetriol; and (c) reacting at least a portion of the 1,2,6-hexanetriol with hydrogen in the presence of the heterogeneous reduction catalyst comprising Pt to produce 1,6-hexanediol, wherein steps b) and c) are conducted in a single reactor. In preferred embodiments, the 1,6-hexanediol is converted to hexamethylenediamine by a chemocatalytic amination reaction.

In another aspect of the invention, the hexamethylenediamine prepared in accordance with the disclosed processes may be converted, according to processes known in the art, to various other industrially significant chemicals and chemical precursors including, for example, nylon 6,6 and monomers for polyurethanes.

Biorenewable sources such as corn grain (maize), sugar beet, sugar cane as well as energy crops, plant biomass, agricultural wastes, forestry residues, sugar processing residues, plant-derived household wastes, municipal waste, spent paper, switch grass, miscanthus, cassaya, trees (hardwood and softwood), vegetation, crop residues (e.g., bagasse and corn stover) are all rich in hexoses, which can be used to produce furfural derivatives, such as 5-(hydroxymethyl) furfural. Hexoses can be readily produced from such carbohydrate sources by hydrolysis. It is also generally known that biomass carbohydrates can be enzymatically converted to glucose, fructose and other sugars. Dehydration of fructose can readily produce furan derivatives such as 5-(hydroxmethyl)furfural. Acid hydrolysis of glucose is also known to produce 5-(hydroxymethyl)furfural; see, for example, U.S. Pat. No. 6,518,440. Various other methods have been developed for producing 5-(hydroxymethyl)furfural including, for example, those described in U.S. Pat. No. 4,533,743 (to Medeiros et al.); U.S. Pat. No. 4,912,237 (to Zeitsch); U.S. Pat. No. 4,971,657 (to Avignon et al.); U.S. Pat. No. 6,743,928 (to Zeitsch); U.S. Pat. No. 2,750,394 (to Peniston); U.S. Pat. No. 2,917,520 (to Cope); U.S. Pat. No. 2,929,823 (to Garber); U.S. Pat. No. 3,118,912 (to Smith); U.S. Pat. No. 4,339,387 (to Fleche et al.); U.S. Pat. No. 4,590,283 (to Gaset et al.); and U.S. Pat. No. 4,740,605 (to Rapp). In the foreign patent literature, see GB 591,858; GB 600,871; and GB 876,463, all of which were published in English. See also, FR 2,663,933; FR 2,664,273; FR 2,669,635; and CA 2,097,812, all of which were published in French. Thus, a variety of carbohydrate sources can be used to produce 5-(hydroxymethyl)furfural by a variety of known techniques.

In some preferred embodiments, the carbohydrate source is glucose, and the glucose is converted to fructose using methods known in the art, such as the industrial process to convert glucose into high-fructose corn syrup. As above described, a variety of processes have been disclosed directed to the production of a furfural substrate (e.g., 5-(hydroxymethyl)furfural) from, for example, glucose or other hexoses.

I. Furfural Substrate and Reduction Thereof

Applicants have discovered that a compound of formula II, below, can be prepared by chemocatalytically reacting a furfural substrate of formula I with hydrogen in the presence of an heterogeneous catalyst comprising platinum (Pt) in accordance with the following overall reaction:

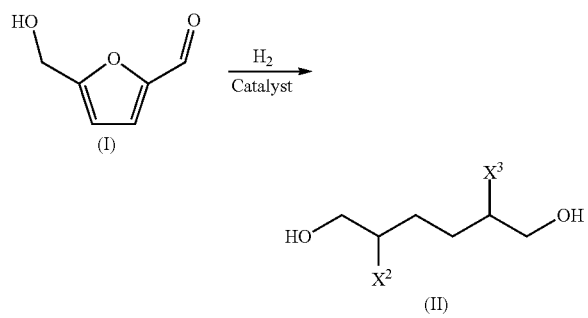

wherein each $X^2$ and $X^3$ is independently hydrogen or hydroxyl. In accordance with various embodiments of the present invention, $X^2$ may be hydrogen or hydroxyl and $X^3$ is, preferably, hydrogen.

In various embodiments, the reaction is conducted in the presence of Pt containing catalysts at temperature(s) in the range of about 60° C. to about 200° C. and pressure(s) in the range of about 200 psig to about 2000 psig.

In accordance with various embodiments of the present invention, a compound of formula IIa can be prepared by chemocatalytically converting 5-(hydroxmethyl)furfural (HMF) to a reaction product comprising the compound of formula IIa by reacting HMF with hydrogen in the presence of catalyst comprising Pt in accordance with the following overall reaction:

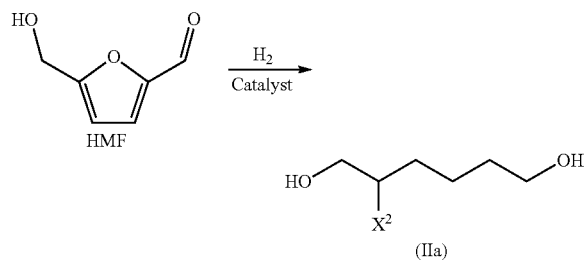

wherein $X^2$ is hydroxyl or hydrogen.

In accordance with further embodiments of the present invention, 5-(hydroxmethyl)furfural is initially reacted with hydrogen in the presence of a catalyst comprising Pt under a first set of reaction conditions to convert at least a portion of the 5-(hydroxmethyl)furfural to 1,2,6-hexanetriol, and at least a portion of the 1,2,6-hexanetriol is subsequently converted to 1,6-hexanediol in the presence of a catalyst comprising Pt under a second set of reaction conditions in accordance with the following overall reaction:

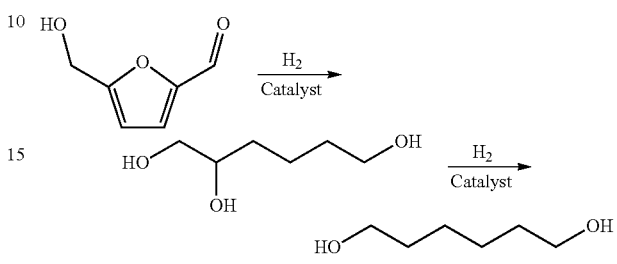

In certain embodiments of the invention, the first reduction reaction to convert 5-(hydroxmethyl)furfural to a reaction product comprising 1,2,6-hexantriol and the second reduction reaction to convert at least a portion of the 1,2,6-hexantriol to 1,6-hexanediol may be accomplished in a single reaction zone wherein the reaction conditions are modified after a defined period of time to effect the conversion of the triol to the diol.

In various other embodiments of the present invention, the first reduction reaction and the second reduction reaction are undertaken in finite zones of a single reactor, e.g., a fixed bed trickle flow reactor, wherein in a first zone is housed a first reduction catalyst operating under reaction conditions to produce a reaction product comprising 1,2,6 hexanetriol and in a second reaction zone is housed a second reduction catalyst operating under reaction conditions to convert at least a portion of the triol to 1,6 hexanediol. In such embodiments, the catalysts may be the same or different and the first set of reaction conditions and the second set of reaction conditions may be the same or different. In some embodiments, the first set of reaction conditions comprises a temperature in the range of about 60° C. to about 200° C. and a pressure in the range of about 200 psig to about 2000 psig. In some embodiments, the second set of reaction conditions comprises a temperature in the range of about 80° C. to about 200° C. and a pressure in the range of about 500 psig to about 2000 psig.

Catalysts suitable for the hydrogenation reactions (reduction catalysts) are particular supported heterogeneous catalysts comprising Pt. In all embodiments of the present invention the catalysts comprise platinum as Pt(0), alone or in combinations with other metals and/or alloys, which is present on at least an external surface of a support (i.e., a surface exposed to the reaction constituents). In accordance with certain embodiments of the present invention, the catalysts employed in the processes comprise Pt and at least one metal selected from the group of Mo, La, Sm, Y, W, and Re (M2). In various embodiments of the invention one or more other d-block metals, one or more rare earth metals (e.g. lanthanides), and/or one or more main group metals (e.g. Al) may also be present in combination with the Pt and M2 combinations. Typically, the total weight of metal(s) is from about 0.1% to about 10%, or from 0.2% to 10%, or from about 0.2% to about 8%, or from about 0.2% to about 5%, of the total weight of the catalyst. In more preferred embodiments the total weight of metal of the catalyst is less than about 4%.

The molar ratio of Pt (M1) to (M2) may vary, for example, from about 20:1 to about 1:10. In various preferred embodiments, the M1:M2 molar ratio is in the range of from about 10:1 to about 1:5. In still more preferred embodiments, the ratio of M1:M2 is in the range of about 8:1 to about 1:2.

In accordance with the present invention, the preferred catalyst is a supported, heterogeneous catalyst wherein the catalysts are on the surface of the support. Suitable supports include, for example, acidic ion-exchange resin, gamma alumina, fluorinated alumina, sulfate or tungstate promoted zirconia, titania, silica, silica promoted alumina, aluminum phosphate, tungsten oxide supported on silica-alumina, acidic clay, supported mineral acid, and zeolites. The support materials may be modified using methods known in the art such as heat treatment, acid treatment or by the introduction of a dopant (for example, metal-doped titanias, metal-doped zirconias (e.g., tungstated-zirconia), metal-doped cerias, and metal-modified niobias). Preferred supports include zirconias, silicas, and zeolites. When a catalyst support is used, the metals may be deposited using procedures known in the art including, but not limited to incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature in the range of about 20° C. to about 120° C. for a period of time ranging from at least about 1 hour to about 24 hours. In these and other embodiments, the catalyst is dried under sub-atmospheric pressure conditions. In various embodiments, the catalyst is reduced after drying (e.g., by flowing 5% $H_2$ in $N_2$ at a temperature of at least about 200° C. for a period of time e.g., at least about 3 hours). Still further, in these and other embodiments, the catalyst is calcined in air at a temperature of at least about 200° C. for a period of time of at least about 3 hours.

The hydrogenation reaction(s) can also be conducted in the presence of a solvent to the furfural substrate. Solvents suitable for use in conjunction with the hydrogenation reaction to convert furfural to reaction product comprising diol or triol may include, for example, water, alcohols, esters, ethers, ketones, or mixtures thereof. In various embodiments, the preferred solvent is water.

In general, the hydrogenation reactions can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in Chemical Process Equipment—Selection and Design, Couper et al., Elsevier 1990, which is incorporated herein by reference. It should be understood that the furfural substrate (e.g., 5-(hydroxymethyl)furfural), hydrogen, any solvent, and the catalyst may be introduced into a suitable reactor separately or in various combinations.

The chemocatalytic conversion of a furfural substrate to 1,6-hexanediol, either as two separate chemocatalytic reduction steps or as a combined chemocatalytic reduction step, may yield a mixture of products. For example, when the furfural substrate is 5-(hydroxmethyl)furfural, the reaction product mixture may include not only 1,6-hexanediol and/or 1,2,6-hexanetriol, but also lesser amounts of 1,5-hexanediol; 1,2,5 hexanetriol; 1,2,5,6-hexanequatrol; 1-hexanol; and 2-hexanol. The production of 1,6-hexanediol from the furfural substrate (e.g., 5-(hydroxmethyl)furfural) is unexpectedly quite facile. In several embodiments, at least 50%, at least 60%, or at least 70% of the product mixture is 1,2,6-hexanetriol. In several embodiments, the production of HDO is at least about 40%, at least about 50% or at least about 60%.

The product mixture may be separated into one or more products by any suitable methods known in the art. In some embodiments, the product mixture can be separated by fractional distillation under subatmospheric pressures. For example, in some embodiments, 1,6-hexanediol can be separated from the product mixture at a temperature between about 90° C. and about 110° C.; 1,2,6-hexanetriol can be separated from the product mixture at a temperature between about 150° C. and 175° C.; 1,2-hexanediol and hexanol can be separated from the product mixture at a temperature between about 100° C. and 125° C. In certain embodiments, 1,2,6-hexanetriol can be isolated from the product mixture, and recycled in a further reduction reaction to produce additional 1,6-hexanediol. The 1,6-hexanediol may be recovered from any remaining other products of the reaction mixture by one or more conventional methods known in the art including, for example, solvent extraction, crystallization or evaporative processes.

In accordance with the present invention the production of HDO from the substrate of formula I can be conducted at reaction temperatures in the range of from about 60° C. to about 200° C., more typically in the range of from about 80° C. to about 200° C. In various preferred embodiments, the step of converting the furfural to 1,2,6-hexanetriol is conducted at reaction temperatures in the range of from about 100° C. to about 140° C. and the conversion of 1,2,6-hexanetriol to 1,6-hexanediol is conducted at reaction temperatures in the range of from about 120° C. to about 180° C. In accordance with the present invention the production of HDO from the substrate of formula I can be conducted at hydrogen pressures in the range of from about 200 psig to about 2000 psig. In various preferred embodiments, the step of converting the furfural to 1,2,6-hexanetriol is conducted at hydrogen pressure in the range of from about 200 psig to about 1000 psig and the conversion of 1,2,6-hexanetriol to 1,6-hexanediol is conducted at hydrogen pressure in the range of from about 200 psig to about 2000 psig.

II. Preparation of Hexamethylenediamine from 1,6-Hexanediol

The preparation of hexamethylenediamine from 1,6-hexanediol may be carried out using procedures known in the art. See, for example, the processes disclosed in U.S. Pat. Nos. 2,754,330; 3,215,742; 3,268,588; and 3,270,059.

When introducing elements of the present invention or the preferred embodiments(s) thereof, the articles "a", "an" are intended to be the singular unless the context admits otherwise and "the" and "said" are intended to mean that there are one or more of the elements. The terms "comprising", "including" and "having" are not intended to be inclusive and use of such terms mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Reactions were conducted in 1 mL glass vials housed in a pressurized vessel in accordance with the procedures described in the examples below. Conversion, product yields and selectivity were determined using ion chromatography with electro-chemical detection.

Example 1

Conversion of Hydroxymethylfurfural to 1,6-Hexanediol

Samples of Silica Cariact Q-10 (Fuji Silysia) support were dried at 60° C. Suitably concentrated aqueous solutions of $(NH_4)_6Mo_7O_{24}$ were added to ~10 mg of solids and agitated to impregnate the supports. The solids were calcined at 600° C. in air for 3 hours. Subsequently, suitably concentrated aqueous solutions of $Pt(NO_3)_2$ were added to ~10 mg of solids and agitated to impregnate the supports. The samples were dried in an oven at 60° C. overnight under a dry air purge. Then reduced at 350° C. under forming gas (5% $H_2$ and 95% $N_2$) atmosphere for 3 hours with 5° C./min temperature ramp rate. The final catalysts were composed of ca. 3.9 wt % Pt & 1.3 wt % Mo.

These catalysts were tested for hydroxymethylfurfural reduction using the following catalyst testing protocol. Catalyst (ca. 8 mg) was weighed into a glass vial insert followed by addition of an aqueous hydroxymethylfurfural solution (200 µl of 0.1 M). The glass vial insert was loaded into a reactor and the reactor was closed. The atmosphere in the reactor was replaced with hydrogen and pressurized to 670 psig at room temperature. Reactor was heated to 160° C. and maintained at the respective temperature for 300 minutes while vials were shaken. After 300 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 1:

TABLE 1

| Entry | Metals | Support | HMF Conversion (%) | 1,2,6-HT Yield (%) | BHMTHF Yield (%) | 1,6-Hexanediol Yield (%), (Selectivity %) | 1,2,6-Hexanetriol Yield (%), (Selectivity %) |
|---|---|---|---|---|---|---|---|
| 1 | Pt—Mo | Silica Cariact | 87 | 12 | 1 | 14 (16) | 48 (50) |

Example 2

Conversion of Hydroxymethylfurfural to 1,2,6-Hexanetriol

Samples of Alumina support were dried at 120° C. Suitably concentrated aqueous solutions of $Pt(NO_3)_2$ were added to ~8 mg of solids and agitated to impregnate the supports. The solids were dried at 120° C. in air for 16 hours. Subsequently, suitably concentrated aqueous solutions of $(NH_4)_6Mo_7O_{24}$ or $La(NO_3)_3$ or $Sm(NO_3)_2$ were added to ~8 mg of solids and agitated to impregnate the supports. The samples were dried in an oven at 120° C. overnight under air. Then calcined at 500° C. under air for 3 hours with 30° C./min temperature ramp rate. The final catalysts were composed of ca. 4 wt % Pt and various M2 loadings (see Table 2).

These catalysts were tested for hydroxymethylfurfural reduction using the following catalyst testing protocol. Catalyst (ca. 8 mg) was weighed into a glass vial insert followed by addition of an aqueous hydroxymethylfurfural solution (250 µl of 0.4 M). The glass vial insert was loaded into a reactor and the reactor was closed. The atmosphere in the reactor was replaced with hydrogen and pressurized to 200 psig at room temperature. Reactor was heated to 120° C. and maintained at the respective temperature for 300 minutes while vials were shaken. After 300 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 2.

TABLE 2

| Entry | Metals | M2:Pt mol:mol | Support | Support Supplier | HMF Conversion (%) | 1,2,6-HT Yield (%), (Selectivity %) |
|---|---|---|---|---|---|---|
| 1 | Pt—Mo | 0.5 | Catalox Alumina SBa-200 | Sasol | 100 | 48 (50) |
| 2 | Pt—Mo | 0.25 | Alumina AL 2100 Davicat | Grace Davison | 100 | 50 (51) |
| 3 | Pt—La | 1 | Catalox Alumina SBa-90 | Sasol | 100 | 51 (50) |
| 4 | Pt—Sm | 1 | Catalox Alumina SBa-90 | Sasol | 100 | 51 (50) |

Example 3

Conversion of 1,2,6-Hexanetriol to 1,6-Hexanediol

Samples of Zirconia SZ 61143 (Saint-Gobain Norpro) support were calcined at 750-800° C. in air for 0.5-2 hours. Suitably concentrated aqueous solutions of $Pt(NO_3)_2$ were added to ~10 mg of solids and agitated to impregnate the supports. The samples were dried in an oven at 60° C. overnight under a dry air purge. Then reduced at 350° C. under forming gas (5% $H_2$ and 95% $N_2$) atmosphere for 3 hours with 5° C./min temperature ramp rate. The final catalysts were composed of ca. 3.9 wt % Pt.

These catalysts were tested for 1,2,6-hexanetriol reduction using the following catalyst testing protocol. Catalyst (ca. 10 mg) was weighed into a glass vial insert followed by addition of an aqueous 1,2,6-hexanetriol solution (200 µl of 0.2 M). The glass vial insert was loaded into a reactor and the reactor was closed. The atmosphere in the reactor was replaced with hydrogen and pressurized to 670 psig at room temperature. Reactor was heated to 160° C. and maintained at the respective temperature for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 3.

TABLE 3

| Entry | Metals | Support | Support Treatment | 1,2,6-Hexanetriol Conversion (%) | 1.6-Hexanediol Yield (%), (Selectivity %) |
|---|---|---|---|---|---|
| 1 | Pt | Zirconia SZ 61143 | 750° C./2 hr | 91 | 61 (68) |
| 2 | Pt | Zirconia SZ 61143 | 800° C./0.5 hr | 95 | 59 (63) |
| 3 | Pt | Zirconia SZ 61143 | 750° C./1 hr | 95 | 58 (62) |

Example 4

Conversion of 1,2,6-Hexanetriol to 1,6-Hexanediol

Samples of Silica Cariact Q-10 (Fuji Silysia) support were dried at 60° C. Suitably concentrated aqueous solutions of $(NH_4)_6Mo_7O_{24}$ or $(NH_4)_{10}W_{12}O_{41}$ were added to ~10 mg of solids and agitated to impregnate the supports. The solids were calcined at 600° C. in air for 3 hours. Subsequently, suitably concentrated aqueous solutions of $Pt(NO_3)_2$ were added to ~10 mg of solids and agitated to impregnate the supports. The samples were dried in an oven at 60° C. overnight under a dry air purge. Then reduced at 350° C. under forming gas (5% $H_2$ and 95% $N_2$) atmosphere for 3 hours with 5° C./min temperature ramp rate. The final catalysts were composed of ca. 3.9 wt % Pt & 0.8 wt % Mo or 3.9 wt % Pt & 1.3 wt % W.

These catalysts were tested for 1,2,6-hexanetriol reduction using the following catalyst testing protocol. Catalyst (ca. 10 mg) was weighed into a glass vial insert followed by addition of an aqueous 1,2,6-hexanetriol solution (200 µl of 0.2 M). The glass vial insert was loaded into a reactor and the reactor was closed. The atmosphere in the reactor was replaced with hydrogen and pressurized to 670 psig at room temperature. Reactor was heated to 160° C. and maintained at the respective temperature for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 4.

TABLE 4

| Entry | Metals | Support | 1,2,6-Hexanetriol Conversion (%) | 1.6-Hexanediol Yield (%), (Selectivity %) |
|---|---|---|---|---|
| 1 | Pt—Mo | Silica Cariact Q-10 | 78 | 55 (69) |
| 2 | Pt—W | Silica Cariact Q-10 | 36 | 33 (92) |

Example 5

Conversion of 1,2,6-Hexanetriol to 1,6,-Hexanediol

Suitably concentrated aqueous solutions of $Pt(NO_3)_2$ and $(NH_4)_6Mo_7O_{24}$ were each added to about 10 mg of solids and agitated to impregnate the supports. The sample was dried in an oven at 60° C. overnight under a dry air purge. The dried sample was then reduced at 500° C. or 350° C. under forming gas (5% $H_2$ and 95% $N_2$) atmosphere for 3 hours with 5° C./min temperature ramp rate. The final catalyst was composed of about 3.9 wt % Pt and 0.2 wt % Mo.

The catalyst was tested for 1,2,6-hexanetriol reduction using the following catalyst testing protocol. Catalyst (ca. 10 mg) was weighed into a glass vial insert followed by addition of an aqueous 1,2,6-hexanetriol solution (200 µl of 0.2 M). The glass vial insert was loaded into a reactor and the reactor was closed. The atmosphere in the reactor was replaced with hydrogen and pressurized to 830 or 670 psig at room temperature. The reactor was heated to 160° C. The temperature was maintained for 5 hours while the vial was shaken. After 5 hours, shaking was stopped and the reactor was cooled to 40° C. Pressure in the reactor was then slowly released. The glass vial insert was removed from the reactor and centrifuged. The clear solution was diluted with deionized water, and analyzed by ion chromatography with electro-chemical detection. The results are summarized in Table 5 below.

TABLE 5

| Entry | Metals | Support | Supplier | 1,2,6-Hexanetriol Conversion (%) | 1.6-Hexanediol Yield (%), |
|---|---|---|---|---|---|
| 1 | Pt—Mo | Silica Cariact G-10 | Fuji Silysia | 54 | 42 |

Example 6

Conversion of 1,2,6-Hexanetriol to 1,6-Hexanediol

Samples of Zeolite (Zeolyst) supports were dried at 60° C. Suitably concentrated aqueous solutions of $(NH_4)_{10}W_{12}O_{41}$ were added to ~10 mg of solids and agitated to impregnate the supports. The solids were calcined at 500° C. in air for 3 hours. Subsequently, suitably concentrated aqueous solutions of $Pt(NO_3)_2$ were added to ~10 mg of solids and agitated to impregnate the supports. The samples were dried in an oven at 60° C. overnight under a dry air purge. Then reduced at 350° C. under forming gas (5% $H_2$ and 95% $N_2$) atmosphere for 3 hours with 5° C./min temperature ramp rate.

These catalysts were tested for 1,2,6-hexanetriol reduction using the following catalyst testing protocol. Catalyst (ca. 10 mg) was weighed into a glass vial insert followed by addition of an aqueous 1,2,6-hexanetriol solution (200 µl of 0.2 M). The glass vial insert was loaded into a reactor and the reactor was closed. The atmosphere in the reactor was replaced with hydrogen and pressurized to 670 psig at room temperature. Reactor was heated to 160° C. and maintained at the respective temperature for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are summarized in Table 6 below.

TABLE 6

| Entry | Metals | M2:Pt mol:mol | Support | 1,2,6-Hexanetriol Conversion (%) | 1,6-Hexanediol Yield (%), (Selectivity %) |
|---|---|---|---|---|---|
| 1 | Pt—W | 0.33 | Zeolite CBV 720 (Y) | 89 | 49 (60) |
| 2 | Pt—W | 0.33 | Zeolite CP811C-300 (Beta) | 100 | 65 (65) |

We claim:

1. A process for preparing a product comprising 1,2,6-hexanetriol, wherein the process comprises reacting 5-(hydroxymethyl)furfural (HMF) with hydrogen in the presence of a heterogeneous catalyst comprising Pt to produce a product comprising 1,2,6-hexanetriol.

2. The process of claim 1, wherein the reaction of the HMF with hydrogen is carried out at a temperature in the range of about 60° C. to about 200° C. and a pressure in the range of from about 200 psig to about 2000 psig.

3. The process of claim 1, wherein the reaction of the HMF with hydrogen is carried out at a temperature in the range of from about 100° C. to about 140° C.

4. The process of claim 1, wherein the heterogeneous catalyst further comprises at least one metal (M2) selected from the group consisting of Mo, La, Sm, Y, W, and Re.

5. The process of claim 4, wherein M2 is W.

6. The process of claim 4, wherein M2 is Mo.

7. The process of claim 4, wherein M2 is La.

8. The process of claim 4, wherein M2 is Sm.

9. The process of claim 4, wherein the molar ratio of Pt to M2 is in the range of from about 20:1 to about 1:10.

10. The process of claim 9, wherein the molar ratio of Pt to M2 is in the range of from about 10:1 to about 1:5.

11. The process of claim 10, wherein the molar ratio of Pt to M2 is in the range of from about 8:1 to about 1:2.

12. The process of claim 1, wherein the heterogeneous catalyst is a supported heterogeneous catalyst.

13. The process of claim 12, wherein the supported heterogeneous catalyst comprises a support selected from the group consisting of acidic ion-exchange resin, gamma alumina, fluorinated alumina, sulfate or tungsten promoted zirconia, titania, silica, silica promoted alumina, aluminum phosphate, tungsten oxide supported on silica-alumina, acidic clay, supported mineral acid and zeolites.

14. The process of claim 12, wherein the supported heterogeneous catalyst comprises a support selected from the group consisting of metal-doped titania, metal-doped zirconia, metal-doped ceria and metal-modified niobia.

15. The process of claim 12, wherein the supported heterogeneous catalyst comprises a support selected from the group consisting of a zirconia, a silica, and a zeolite.

16. The process of claim 4, wherein the heterogeneous catalyst is a supported heterogeneous catalyst.

17. The process of claim 16, wherein the supported heterogeneous catalyst comprises a support selected from the group consisting of acidic ion-exchange resin, gamma alumina, fluorinated alumina, sulfate or tungsten promoted zirconia, titania, silica, silica promoted alumina, aluminum phosphate, tungsten oxide supported on silica-alumina, acidic clay, supported mineral acid and zeolites.

18. The process of claim 16, wherein the supported heterogeneous catalyst comprises a support selected from the group consisting of metal-doped titania, metal-doped zirconia, metal-doped ceria and metal-modified niobia.

19. The process of claim 16, wherein the supported heterogeneous catalyst comprises a support selected from the group consisting of a zirconia, a silica, and a zeolite.

20. The process of claim 16, wherein the heterogeneous catalyst comprises a total weight of metal that is in the range of from about 0.1% to about 10% of the total weight of the catalyst.

21. The process of claim 16, wherein the heterogeneous catalyst comprises a total weight of metal that is in the range of from about 0.2% to about 8% of the total weight of the catalyst.

22. The process of claim 16, wherein the catalyst comprises a total weight of metal that is in the range of from about 0.2% to about 5% of the total weight of the catalyst.

23. The process of claim 16, wherein the heterogeneous catalyst comprises a total weight of metal that is less than about 4% of the total weight of the catalyst.

24. The process of claim 1, wherein the process is conducted in the presence of a solvent selected from the group consisting of water, an alcohol, an ester, an ether, a ketone, and a mixture thereof.

25. The process of claim 24, wherein the solvent comprises water.

26. The process of claim 4, wherein the process is conducted in the presence of a solvent selected from the group consisting of water, an alcohol, an ester, an ether, a ketone, and a mixture thereof.

27. The process of claim 26, wherein the solvent comprises water.

* * * * *